United States Patent
Laskoski et al.

(10) Patent No.: US 8,362,239 B2
(45) Date of Patent: Jan. 29, 2013

(54) HETEROAROMATIC PHTHALONITRILES

(75) Inventors: Matthew Laskoski, Springfield, VA (US); Teddy M Keller, Fairfax Station, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/479,432

(22) Filed: May 24, 2012

(65) Prior Publication Data
US 2012/0232270 A1 Sep. 13, 2012

Related U.S. Application Data

(62) Division of application No. 12/616,836, filed on Nov. 12, 2009, now Pat. No. 8,222,403.

(51) Int. Cl.
*C07D 291/00* (2006.01)
*C08G 65/40* (2006.01)
*C08G 79/02* (2006.01)

(52) U.S. Cl. ......... 544/1; 546/155; 546/296; 525/331.3; 524/431; 524/432; 528/423; 528/425; 528/373

(58) Field of Classification Search ...... 544/1; 546/155, 546/296; 525/331.3; 524/431, 432; 252/62.51, 252/62.55; 528/423, 425, 373
See application file for complete search history.

(56) References Cited

PUBLICATIONS

Rossom et al; Effficient fragment coupling appraoches toward large Oxacalix[n] arenes (n=6,8); Org. Lett., 11, 1681-1684, (Jan. 2009).*

\* cited by examiner

*Primary Examiner* — Duc Truong
(74) *Attorney, Agent, or Firm* — Amy L. Ressing; Joseph T. Grunkemeyer

(57) ABSTRACT

Disclosed are an oligomer and a phthalonitrile monomer having the formulas:

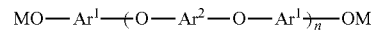
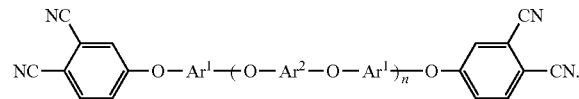

M is a metal or H. The value n is an integer greater than or equal to 1 for the oligomer and greater than or equal to 0 for the phthalonitrile monomer. $Ar^1$ and $Ar^2$ are independently selected aromatic- or heterocyclic-containing groups. $Ar^1$, $Ar^2$, or both are heteroaromatic or heterocyclic groups containing a nitrogen, sulfur, or oxygen heteroatom. Also disclosed are thermosets and pyrolyzed materials made from the phthalonitrile monomer.

6 Claims, 2 Drawing Sheets

HETEROAROMATIC PHTHALONITRILES

This application is a divisional application of U.S. patent application Ser. No. 12/616,836, allowed and filed on Nov. 12, 2009 now U.S. Pat. No. 8,222,403.

TECHNICAL FIELD

The present disclosure is generally related to oligomers containing heteroaromatic groups and phthalonitriles, thermosets, and other materials made therefrom.

DESCRIPTION OF RELATED ART

Phthalonitrile resins show potential as matrix materials for advanced composites. The phthalonitrile monomers polymerize through the cyano groups with the aid of an appropriate curing agent to yield a crosslinked polymeric network with high thermal and oxidative stabilities. These polymers are obtained by heating the phthalonitrile monomers and a small amount of curing additive in the melt-state above 200° C. for extended periods of time. Phthalonitrile monomers and phthalonitrile polymers of various types are described generally in U.S. Pat. Nos. 3,730,946, 3,763,210, 3,787,475, 3,869,499, 3,972,902, 4,209,458, 4,223,123, 4,226,801, 4,234,712, 4,238,601, 4,259,471, 4,304,896, 4,307,035, 4,315,093, 4,351,776, 4,408,035, 4,409,382, 4,410,676, 5,003,039, 5,003,078, 5,004,801, 5,132,396, 5,159,054, 5,202,414, 5,208,318, 5,237,045, 5,242,755, 5,247,060, 5,292,854, 5,304,625, 5,350,828, 5,352,760, 5,389,441, 5,464,926, 5,925,475, 5,965,268, 6,001,926, 6,297,298, 6,756,470, 6,891,014, 7,452,959, 7,511,113, and U.S. Pat. Appl. Pub. Nos. 2008/0255287 and 2009/0069484 (all publications and patent documents referenced throughout this application are incorporated herein by reference.)

Previously, a variety of phthalonitrile monomers containing aromatic ether, thioether, imide and sulfone linkages between the terminal phthalonitrile units have been synthesized and cured or converted to crosslinked/networked polymers. The cure reaction of these monomers has been investigated by a variety of curing additives such as organic amines, strong organic acids, strong organic acids/amine salts, metallic salts and metals. When post-cured at elevated temperatures to about 400° C., the thermoset shows excellent long-term thermal and oxidative stabilities to temperatures approaching 375° C. In addition, the high aromatic content of the thermoset affords a high char yield (80-90%) when pyrolyzed to 1000° C. under inert conditions. The high thermal stability and the ability to form a high char yield upon pyrolysis contribute to the outstanding fire performance of the phthalonitrile polymer. For instance, the fire performance of phthalonitrile-carbon and phthalonitrile-glass composites are superior to that of other thermoset-based composites currently in use for aerospace, ship and submarine applications. The phthalonitriles are the only polymeric material that meets MIL-STD-2031 for usage inside of a submarine and are being considered for usage below deck on warships.

High performance polymers have been converted into carbon nanotube and carbon nanotube-metal nanoparticle compositions. The approach is that shaped solid components, fibers, and films can be fabricated from the melt or amorphous state of the precursor compounds. Moreover, the resulting polymer or charred materials containing elemental Fe, Ni, and/or Co nanoparticles dispersed throughout the polymeric and carbon domains exhibit magnetic properties (attracted to a bar magnet). The magnetic and electrical properties in these systems can be fine-tuned as a function of heat treatment, time, and temperature. Broad methods for the synthesis of the various carbon nanotube and carbon nanotube-metal nanoparticle compositions from commercially available resins and high performance polymers are disclosed in U.S. Pat. No. 6,770,583, 6,846,345, 7,579,424, and U.S. Pat. Appl. Pub. Nos. 2006/0130609 and 2008/0255287. Moreover, materials (polyacrylonitrile and the pitches) that are presently being used to fabricate commercial carbon and graphitic fibers can be converted into carbon nanotube and carbon nanotube-metal nanoparticle containing fibers. Magnetic carbon nanotube fibers have been realized for potential electrical and magnetic device applications. Phenolic resins (an inexpensive source of carbon) can be converted into a carbon nanotube carbonaceous composition. High performance and high temperature polymers such as the polyimides, epoxies, phthalonitriles, cyanate ester resins, polyaryletheretherketone (PEEK), and polyaromaticsulfones (PES) are commercially available and can be used in the formulation of a bulk solid, fiber, and/or film-containing carbon nanotube composition. Depending on the formulation parameters, the physical properties can be varied for potential magnetic, electrical, structural, catalytic, and medical applications. The approach allows for the in situ formation of metal nanoparticles and carbon nanotubes-metal nanoparticles within a high performance polymeric system and carbonaceous composition, respectively. The ability to control the amount and size of the metal nanoparticles within the polymeric and carbon nanotube composition can be achieved. Control of the carbon nanotube and metal nanoparticle concentration is important for various potential applications. Upon gelation, the mobility of the metal particles will be reduced and the metal particles will be less free to move within the developing solid composition. Besides Fe, Ni, and Co systems, it is believed that any transition metal salt, organometallic compound, or metal alloy that decomposes into metal atoms such as Ru, Os, Mo, W, etc., can be used as the metal source for the formation of carbon nanotubes.

BRIEF SUMMARY

Disclosed herein is an oligomer having the formula:

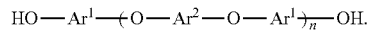

M is a metal or H. The value n is an integer greater than or equal to 1; $Ar^1$ and $Ar^2$ are independently selected aromatic- or heterocyclic-containing groups; and $Ar^1$, $Ar^2$, or both are heteroaromatic or heterocyclic groups containing a nitrogen, sulfur, or oxygen heteroatom.

Also disclosed herein is a phthalonitrile monomer having the formula:

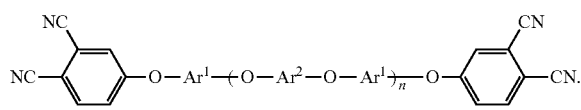

The value n is an integer greater than or equal to 0 and $Ar^1$ and $Ar^2$ are independently selected aromatic- or heterocyclic-containing groups. If n is greater than 0, then $Ar^1$, $Ar^2$, or both are heteroaromatic or heterocyclic groups containing a nitrogen, sulfur, or oxygen heteroatom. If n is 0, then $Ar^1$ is a heteroaromatic or heterocyclic group containing a nitrogen, sulfur, or oxygen heteroatom.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

Figure 1:
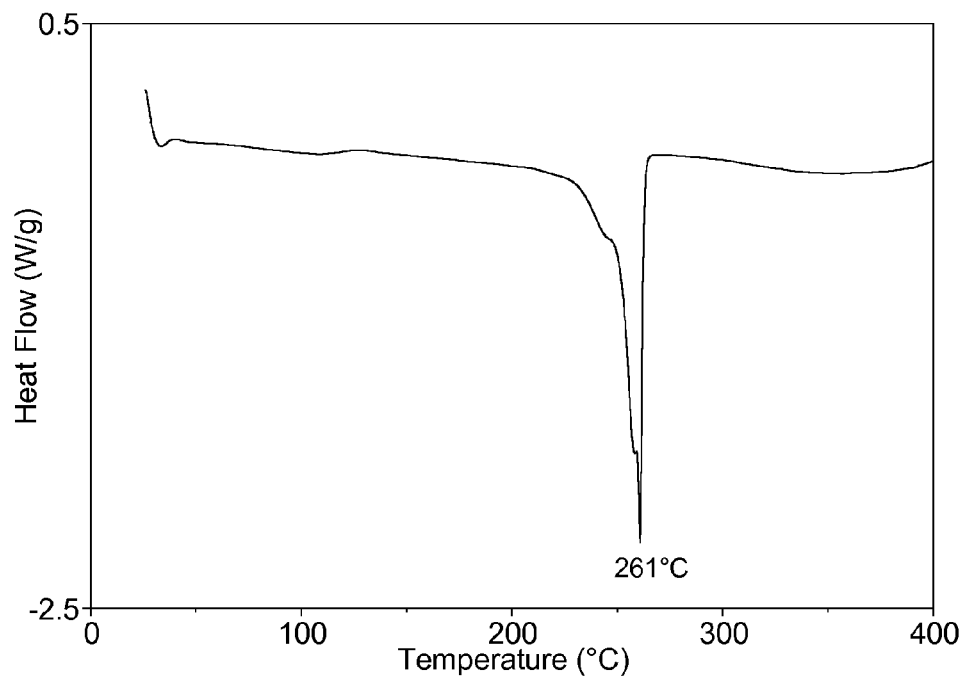
FIG. 1 shows a DSC of the phthalonitrile of Example 1 heated with 5% p-BAPS.

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed are methods related to the synthesis and polymerization of heteroaromatic- and heterocyclic-containing phthalonitriles and low melting oligomeric heteroaromatic and/or heterocyclic-containing phthalonitriles in which the nitrogen, oxygen, and/or sulfur heteroaromatic and/or heterocyclic moieties or linkages are situated between the terminal phthalonitrile units, their conversion to high temperature thermosets, and the thermal treatment and carbonization to carbon nanotube-containing carbonaceous solids. The simple heteroaromatic- and heterocyclic-containing phthalonitriles are synthesized from the corresponding dihydroxyl heteroaromatic or heterocyclic compounds. The oligomeric heteroaromatic- and/or heterocyclic-containing phthalonitriles are synthesized from the corresponding oligomeric dihydroxyl-terminated compounds. The nitrogen, oxygen, and/or sulfur heteroaromatic- and/or heterocyclic-containing phthalonitrile monomers upon polymerization to thermosets may show superior thermal, thermo-oxidative, and flammability properties and can withstand continuous high temperatures (300-375° C.) in an oxidative environment such as air for extended periods. To date, current oligomeric phthalonitrile polymers have melting points between 50 and 260° C. with the polymerization occurring in excess of 200° C. The use of oligomeric heteroaromatic- and heterocyclic-containing phthalonitriles, which melt at relative low temperatures, to obtain thermosetting polymeric materials with high thermo-oxidative properties may be advantageous from a processing standpoint. Precursor resins are useful in composite fabrication by a variety of methods such as infusion, resin transfer molding, and prepreg consolidation. The phthalonitriles may be useful for numerous aerospace and electronic applications due to their thermal and oxidative properties, processability, and low water absorption relative to other high temperature polymers such as polyimides. Furthermore, resins with a large window between the melting point and the cure temperature may be desirable to control the viscosity and the rate of curing. With the phthalonitrile monomers disclosed herein, processability to shaped composite components may be achieved in non-autoclave conditions potentially above 70° C. and by cost effective methods; the nitrogen, oxygen, and sulfur heteroaromatic and heterocyclic based phthalonitriles may show enhanced adhesive properties. By incorporating heteroaromatics and/or heterocyclics into the backbone or the interconnecting moiety between the terminal phthalonitrile units, the adhesive properties of the high temperature thermoset may be enhanced relative to an aromatic system containing only carbon.

Also disclosed is the formation of the thermoset in the presence of a small quantity of an organometallic compound and/or metal salt followed by thermal treatment to temperatures at least to, for example, 1300° C. in an inert atmosphere resulting in the formation of nitrogen, oxygen, and/or sulfur-containing carbon nanotubes (CNTs) and/or carbon nanofibers (CNFs) embedded in a carbonaceous solid matrix. The key to the formation of the CNTs/CNFs is the decomposition of the organometallic compound or metal salt into metal nanoparticles, which interact with the developing fused, heteroaromatic and/or heterocyclic ring system during the polymerization and carbonization processes. The heteroaromatic/heterocyclic precursor phthalonitrile materials are either physically mixed or coated in solution with organometallic compounds or metal salts that decompose upon thermal treatment ultimately yielding metal nanoparticles. The resulting metal nanoparticle compositions upon heating to temperatures above 500° C. may afford CNT/CNF-metal nanoparticle compositions. The amount of CNTs/CNFs and metal nanoparticles depends on the temperature exposure and concentration of metal nanoparticles, respectively. Carbon nanotube fibers and composite matrices can be formulated by the method of this invention. Precursor organometallic or metal salts to Fe, Ni, and Co have been used in our studies. However, any transition metal that has been shown to lead to the formation of CNTs from organic vapors, thermal deposition of hydrocarbons, and arc discharge can probably be used to form an organometallic precursor with the phthalonitriles of this invention followed by thermal decomposition of the metallic or organometallic unit to metal nanoparticles and formation of carbon nanotubes in the bulk of polymeric and carbon systems, respectively. Depending on the conditions, CNTs/CNFs will form either in amorphous carbon or in a highly ordered graphitic domain. Films, fibers, and shaped components can be obtained. Carbon nanotube fibers may be made from inexpensive precursors that are presently being used to spin commercial fibers. The CNT/CNF compositions contain metal nanoparticles in varying amounts depending on the original organometallic concentration or metal salt in the precursor heteroaromatic and/or heterocyclic phthalonitriles. Moreover, the CNT/CNF compositions exhibit magnetic and electrical properties, which can be fine-tuned. The method can allow for the formation in situ of nitrogen, oxygen, and/or sulfur-containing carbon nanotubes in a carbonaceous solid matrix. The materials can potentially be useful for structural, air filtration, microelectronic, battery, fuel cell electrode, hydrogen storage, and catalytic applications. X-ray diffraction studies show that CNTs and/or CNFs are being formed in the carbonaceous media and their concentration will depend on the thermal exposure condition.

To enhance the uptake of gaseous materials, the incorporation of heteroatoms such as nitrogen, oxygen, and/or sulfur into the CNTs/CNFs may disrupt the aromaticity of a pure CNT or CNF and enhance the uptake of gaseous materials such as hydrogen and toxins. The ability to store hydrogen in large quantities in lightweight materials is desirable for fuel cells for automobiles and other vehicles. A low melt viscosity phthalonitrile resin enables the large-scale production of shaped CNT/CNF-containing carbonaceous components. Low melting oligomeric phthalonitrile monomers and curing additives (metal carbonyl and other metal salts) have been shown to enhance the overall physical properties and processability of phthalonitriles.

The syntheses of example simple heteroaromatic- and heterocyclic-containing phthalonitriles are shown below (Eq. (1) nitrogen containing heteroaromatic; Eq. (2) sulfur containing heterocyclic). As used herein heteroaromatic and heterocyclic refers to any aromatic or cyclic compound in which at least one ring carbon atom is changed to a nitrogen, oxygen, or sulfur atom. The rings may by substituted or unsubstituted and contain single rings or multiple fused or nonfused rings. Heteroaromatics and heterocyclics may be referred to collectively as "heteroaromatics" for simplicity. The term "aromatic" may also include heteroaromatics. In the reactions shown below, a heteroaromatic diol is reacted with 4-nitrophthalonitrile to form the phthalonitrile-terminated monomer. The reaction may be performed in the presence of a potassium carbonate catalyst. Other carbonates or bases may be used, as may any method disclosed in the above-referenced phthalonitrile patents.

Eq. (2)

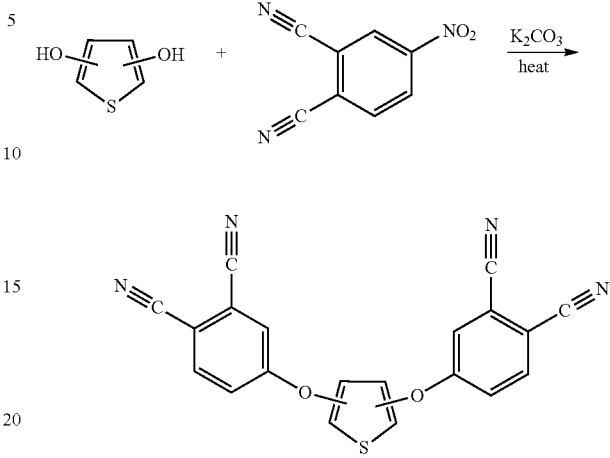

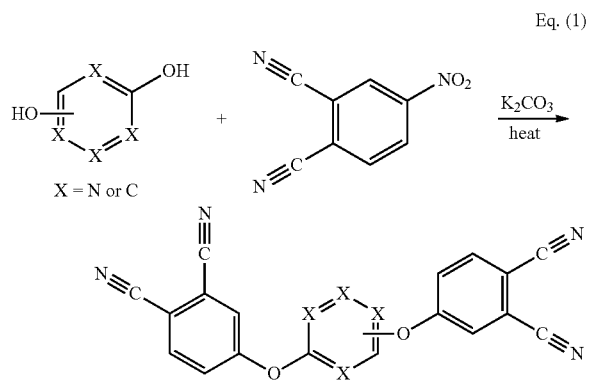

Eq. (1)

The low melting oligomeric heteroaromatic- and/or heterocyclic-containing phthalonitriles can exhibit a larger processing window useful for composite and device fabrication. The synthesis of such oligomers is shown in Eq. (3). The term "oligomeric" means that more than one compound is formed during the synthesis of 1 with the average molecular weight dependent on the ratios of reactants, 2 and 3, used. The diol and dihalo may be reacted in the presence of a copper compound and a base or by other methods known in the art, such as those disclosed in the above-referenced patents. An excess of diol is used so that the intermediate may be terminated as the metal salt of a diol, where n is 1, 2, or more.

Eq. (3)

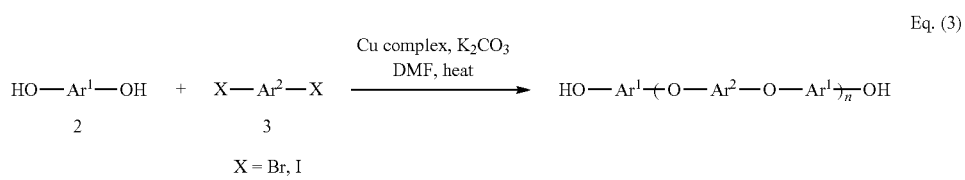

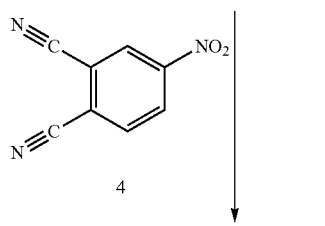

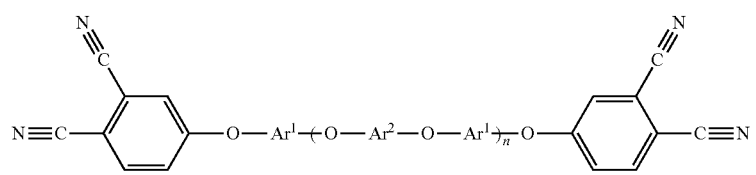

The synthesis of a series of oligomeric heteroaromatic- and/or heterocyclic-containing phthalonitriles 1, which contain nitrogen, oxygen, and/or sulfur atom(s) unit in the backbone or interconnecting unit between the terminal phthalonitriles, may be achieved, for example, by a modified Ullmann synthesis. The potassium diphenolate-terminated intermediate was prepared from the reaction of 2 and 3 in the presence of potassium carbonate as the base and a copper (I) complex in a DMF/toluene solvent mixture. This allows the azeotropic distillation of the water formed as a by-product in the reaction at temperatures between 135 and 145° C. When no more water is observed being azeotropically distilled and infrared (IR) spectroscopy confirms the desired oligomeric product, the reaction may be considered complete. Further reaction of the potassium diphenolate-terminated intermediate with 4-nitrophthalonitrile 4 can afford the oligomeric phthalonitriles 1 in 90-95% yields, which may be readily soluble in common organic solvents such as toluene, DMF, acetone, methylene chloride, ether, and chloroform. The structures of the monomers 1 were confirmed by IR and $^1$H-NMR spectroscopy. The length of the spacer between the terminal phthalonitrile groups can be varied by changing the ratio between 2 (excess) and 3. Oligomeric phthalonitrile resins 1 (n≧1) generally have melting points between 70 and 100° C., whereas the simple phthalonitrile (n=0) may have a melting point greater than 250° C. Several heteroaromatic and heterocyclic phthalonitriles 1 have been synthesized by this method and the structures are shown below.

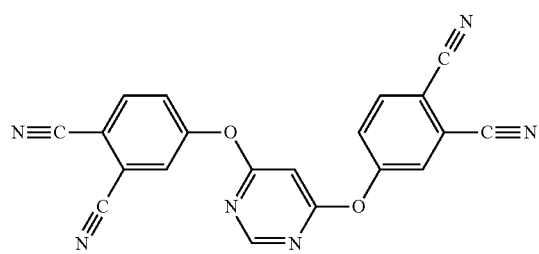

Eq. (4)

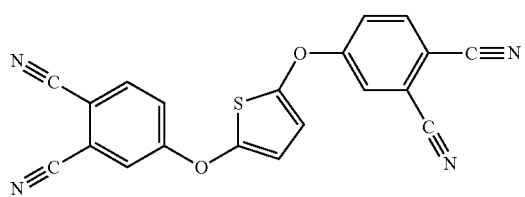

Eq. (5)

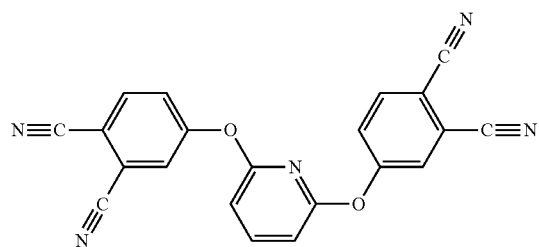

Eq. (6)

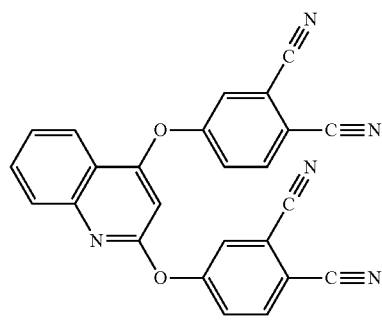

Eq. (7)

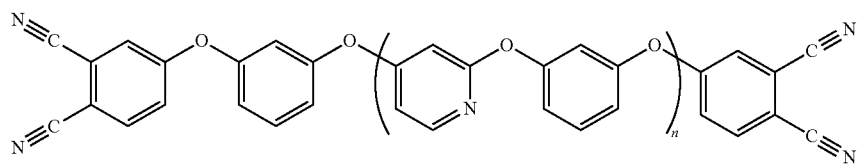

Eq. (8)

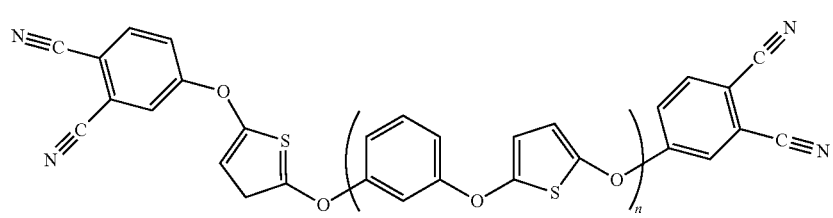

Eq. (9)

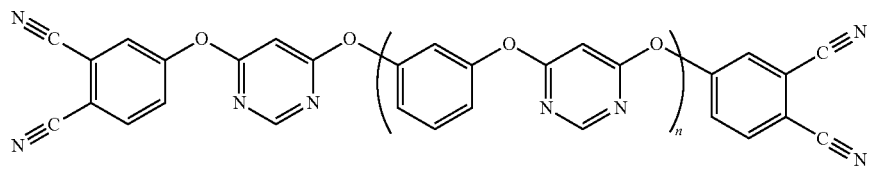

Eq. (10)

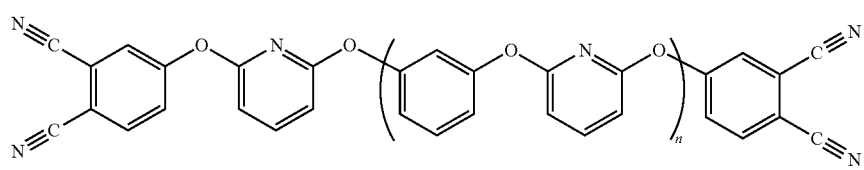

Eq. (11)

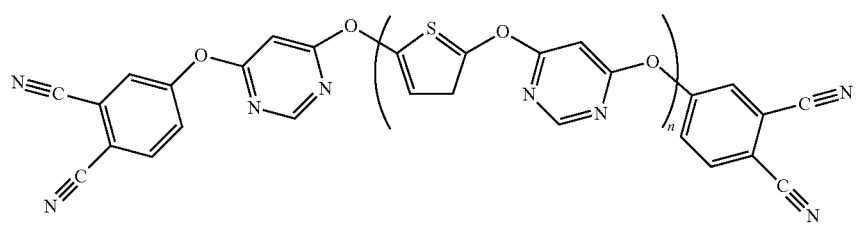

Eq. (12)

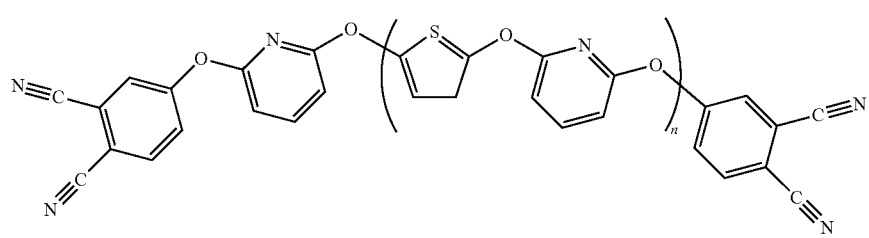

Eq. (13)

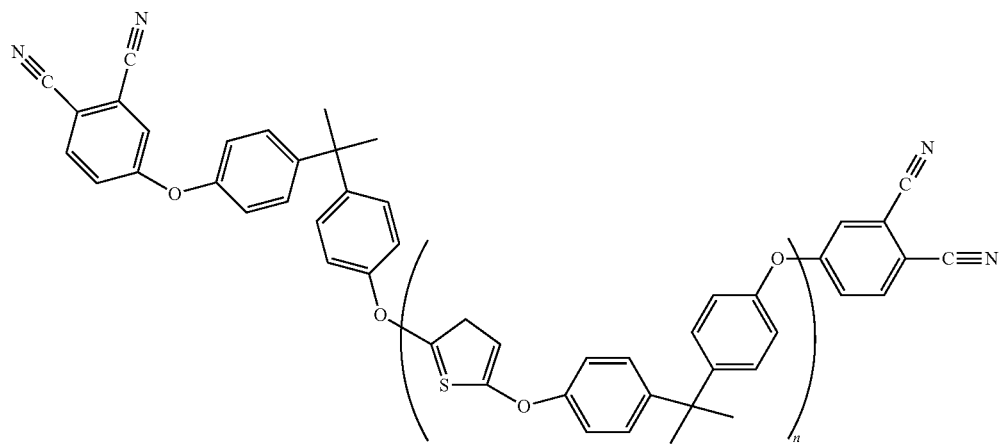

Eq. (14)

The phthalonitriles may be cured to a thermoset. The thermoset will generally be made from a range of oligomer sizes having different values of n, but may be described by the average value of n. For example, a 3:2 ratio of diol to dihalo will produce an n of 2, though longer and shorter oligomers may be present. An aromatic amine may be used as a curing agent, or any curing agent disclosed in the above-referenced phthalonitrile patents. The curing may also be done after combining the monomer with a filler, including but are not limited to, carbon nanotubes, hydrated aluminum silicate, carbon nanofibers, zinc oxide, or boric acid.

The nitrogen, oxygen, and sulfur heteroaromatic-containing phthalonitriles may be converted to a CNT- and/or CNF-containing carbonaceous solid by heating the phthalonitrile in the presence of a small quantity of a metal salt such as $Fe_2(CO)_9$, $Ni(cyclooctadiene)_2$ ($Ni(COD)_2$), or $Co_2(CO)_8$ resulting in initially curing to the thermoset followed by thermal treatment to elevated temperatures where CNT/CNF formation readily occurs during carbonization above 700° C. CNTs may be formed when magnetic nanoparticles are formed. The typical experiments are as follows: (1) the precursor materials and various amounts of a metal salt are mixed in methylene chloride or hexane with stirring followed by concentration to dryness, or (2) the precursor materials and various amounts of an organometallic compound or metal salt are thoroughly mixed physically in a solid composition. The compositions formulated by either of the two methods are heated to various temperatures up to, for example, 1300° C. The organometallic compound or metal salt decomposes resulting in the formation of metal atoms, clusters, and/or nanoparticles, which are responsible for the development and formation of the carbon nanotubes. The properties of the carbon nanotube-metal nanoparticle composition will depend on the heat treatment, time of thermal exposure, and concentration of metal particles.

Heat treatment of the phthalonitrile precursor-metal systems under inert conditions at 300-500° C. may result in the formation of elemental metal (Fe, Ni, and Co) in an insulating polymeric matrix as determined by the attraction of the composition to a magnet. The magnetic compositions may retain excellent structural integrity. The polymers may also exhibit high thermal stability. Upon polymerization, the useful thermal properties (300-375° C.) exhibited by the phthalonitrile polymers may be retained. The different polymers with various concentrations of metal particle sizes will have distinct properties, which would be expected to affect the characteristics of the final metal containing systems.

Depending on the heteroaromatic and/or heterocyclic phthalonitrile precursor system and application, fibers, films, powders, and matrix components can be formulated by the method. The metal nanoparticle, carbon nanotube, carbon nanofiber, and carbon nanotube-metal nanoparticle compositions could have novel magnetic, electrical, catalytic, and structural properties.

Only metal nanoparticles that are generated in situ and chemically interact with the precursor organic materials during the heat treatment can be used to form the nitrogen, oxygen, and/or sulfur-containing-CNTs/CNFs within the charred carbonaceous compositions. The amount of nitrogen, oxygen, and/or sulfur incorporated into the CNT carbonaceous solids will depend on the precursor phthalonitrile and the char yield. The metal nanoparticle size and concentration can be readily changed by varying the concentration of precursor heteroaromatic and/or heterocyclic phthalonitrile and organometallic compound or metal salt. Metals that are not magnetic afford metal nanoparticles embedded within the carbonaceous domain. Fe, Ni, and Co may afford high yield of CNTs/CNFs within the carbonaceous solid and containing some nitrogen, oxygen, and/or sulfur atoms from the incorporation of the heteroatoms into the CNT structure. Moreover, XPS experiments have shown the presence of the heteroatoms within the carbonaceous solids. Similar studies on crystalline calcined (oxygen purification to remove the amorphous carbon, such as disclosed in U.S. Pat. Appl. Pub. No. 2008/0292530) samples show the presence of the heteroatoms. The choice of precursor materials (metal source and phthalonitrile) may allow varying the amount of heteroatoms and metal nanoparticles within the CNT and/or CNF-containing carbonaceous solids.

The following examples are given to illustrate specific applications. These specific examples are not intended to limit the scope of the disclosure in this application. Specifics regarding any example may be applicant to other or all embodiments.

EXAMPLE 1

Synthesis of a heteroaromatic phthalonitrile based on 1,3-dihydroxypyrimidine and 4-nitrophthalonitrile—To a 100 mL, three-necked flask fitted with a thermometer, a Dean-Stark trap with condenser, and a nitrogen inlet were added 1,3-dihydroxypyrimidine (5.00 g, 44.6 mmol), 4-nitrophthalonitrile (15.83 g, 91.4 mmol), powdered anhydrous $K_2CO_3$ (13.0 g, 94.2 mmol), and N,N-dimethylformamide (DMF) (100 mL). The resulting mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the heteroaromatic phthalonitrile (14.4 g, 90% yield). IR [$cm^{-1}$]: δ 3058 (C═CH), 2231 (C≡N), 1610 (C═N), 1589 (C═C), 1491 (aromatic), 1281 ($CH_3$), 1248 (C—O), 1173 (C—O), 970 (C—O), 834 (aromatic).

EXAMPLE 2

Curing of a heteroaromatic phthalonitrile based on 1,3-dihydroxypyrimidine and 4-nitrophthalonitrile with an aromatic amine—Samples containing the heteroaromatic phthalonitrile from Example 1 and 2-3 weight % of bis(4-[4-aminophenoxy]phenyl)sulfone (p-BPAS) or 1,3-bis(3-aminophenoxy)benzene (m-APB) were stirred at 250° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 450° C. in air.

A polymerization study of the phthalonitrile was achieved by DSC analyses (FIG. 1) up to 400° C. in the presence of 5 weight % of p-BAPS to afford the corresponding thermoset. The monomer exhibited a melting point at 261° C. and an exothermic transition peaking at about 270° C. attributed to the softening from the amorphous phase and to the reaction with p-BAPS, respectively.

EXAMPLE 3

Synthesis of a heteroaromatic phthalonitrile based on 1,3-quinolinediol and 4-nitrophthalonitrile—To a 100 mL, three-necked flask fitted with a thermometer, a Dean-Stark trap with condenser, and a nitrogen inlet were added 1,3-dihydroxypyrimidine (3.764 g, 23.3 mmol), 4-nitrophthalonitrile (8.17 g, 47.2 mmol), powdered anhydrous $K_2CO_3$ (10.00 g, 72.5 mmol), and N,N-dimethylformamide (DMF) (70 mL). The resulting mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the heteroaromatic phthalonitrile (8.88 g, 92% yield). IR [$cm^{-1}$]: δ 3060 (C═CH), 2232 (C≡N), 1605 (C═N), 1589 (C═C), 1491 (aromatic), 1281 ($CH_3$), 1248 (C—O), 1173 (C—O), 970 (C—O), 833 (aromatic).

EXAMPLE 4

Curing of a heteroaromatic phthalonitrile based on 1,3-quinolinediol and 4-nitrophthalonitrile with an aromatic amine—Samples containing the heteroaromatic phthalonitrile from Example 3 and 2-3 weight % of p-BPAS or m-APB were stirred at 250° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 470° C. in air.

EXAMPLE 5

Synthesis of a heteroaromatic phthalonitrile based on 2,6-dihydroxypyridine and 4-nitrophthalonitrile—To a 100 mL, three-necked flask fitted with a thermometer, a Dean-Stark trap with condenser, and a nitrogen inlet were added 2,6-dihydroxypyridine (5.00 g, 45.4 mmol), 4-nitrophthalonitrile (15.7 g, 91.0 mmol), powdered anhydrous $K_2CO_3$ (10.00 g, 72.5 mmol), and N,N-dimethylformamide (DMF) (100 mL). The resulting mixture was heated at 80° C. for 6-8 h. The mixture was allowed to cool to ambient temperature and poured into a 5% aqueous HCl solution resulting in the formation of a solid. The material was broken up and collected using a Buchner funnel. The white solid was washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the heteroaromatic phthalonitrile (13.1 g, 80% yield). IR [cm$^{-1}$]: δ 3060 (C=CH), 2230 (CN), 1605 (C=N), 1590 (C=C), 1491 (aromatic), 1281 (CH$_3$), 1248 (C—O), 1173 (C—O), 970 (C—O), 832 (aromatic).

EXAMPLE 6

Curing of a heteroaromatic phthalonitrile based on 2,6-dihydroxypyridine and 4-nitrophthalonitrile with an aromatic amine—Samples containing the heteroaromatic phthalonitrile from Example 5 and 2-3 weight % of p-BPAS or m-APB were stirred at 250° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 470° C. in air.

EXAMPLE 7

Synthesis of a heteroaromatic phthalonitrile based on 1,3-dihydroxythiophene and 4-nitrophthalonitrile—To a 100 mL, three-necked flask fitted with a thermometer, a Dean-Stark trap with condenser, and a nitrogen inlet were added 1,3-dihydroxythiophene (5.00 g, 43.1 mmol), 4-nitrophthalonitrile (14.9 g, 86.1 mmol), powdered anhydrous K$_2$CO$_3$ (14.8 g, 108 mmol), and N,N-dimethylformamide (DMF) (100 mL). The resulting mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the heteroaromatic phthalonitrile (13.5 g, 86% yield). IR [cm$^{-1}$]: δ 3060 (C=CH), 2230 (C=N), 1605 (C=N), 1590 (C=C), 1529 (S—C), 1491 (aromatic), 1410 (S—C), 1281 (CH$_3$), 1248 (C—O), 1173 (C—O), 970 (C—O), 832 (aromatic).

EXAMPLE 8

Curing of a heteroaromatic phthalonitrile based on 1,3-dihydroxypyridine and 4-nitrophthalonitrile with an aromatic amine—Samples containing the heteroaromatic phthalonitrile from Example 7 and 2-3 weight % of p-BPAS or m-APB were stirred at 250° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 470° C. in air.

EXAMPLE 9

Formulation of carbon nanotubes with a heteroaromatic phthalonitrile based on 1,3-dihydroxypyrimidine and 4-nitrophthalonitrile in a solvent—To a mixture of the heteroaromatic phthalonitrile from Example 1 in an appropriate solvent was added various amounts of carbon nanotubes (0.01 to 20 weight %). The mixture was thoroughly mixed. The solvent was removed and the mixture was heated and degassed at 200° C. Then 3 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric compositions exhibited excellent thermal and oxidative stability up to 425-450° C. before any weight loss was detected. Catastrophic decomposition occurred after 500° C. in air.

EXAMPLE 10

Formulation of clay with a heteroaromatic phthalonitrile based on 1,3-dihydroxypyrimidine and 4-nitrophthalonitrile in a solvent—To a mixture of the heteroaromatic phthalonitrile from Example 1 in an appropriate solvent was added various amount of clay (hydrated aluminum silicate, 0.01 to 20 weight %). The resulting mixtures were thoroughly mixed. The solvent was removed and the mixture was heated and degassed at 200° C. Then 3-4 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 450° C. before any weight loss was detected. Catastrophic decomposition occurred after 490° C. in air.

EXAMPLE 11

Formulation of carbon nanofibers with a heteroaromatic phthalonitrile based on 1,3-dihydroxypyrimidine and 4-nitrophthalonitrile in a solvent—To a mixture of the heteroaromatic phthalonitrile from Example 1 in an appropriate solvent was added various amounts of carbon nanofibers (0.01 to 20 weight %). The mixtures were thoroughly mixed by stirring. The solvent was removed and the mixture was heated and degassed at 200° C. Then 4 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 425-450° C. before any weight loss was detected. Catastrophic decomposition occurred after 500° C. in air.

EXAMPLE 12

Formulation of a metal oxide with heteroaromatic phthalonitrile based on 1,3-dihydroxypyrimidine and 4-nitrophthalonitrile n a solvent—To a mixture of the heteroaromatic phthalonitrile from Example 1 in an appropriate solvent was added various amount of powdered zinc oxide (0.01 to 20 weight %) with thorough mixing. The solvent was removed and the mixture was heated and degassed at 200° C. Then 4-5 weight % of p-BPAS or m-APB was stirred in at 200° C. for 2 minutes and the mixture cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 450° C. before a weight loss was detected. Catastrophic decomposition occurred after 500° C. in air.

EXAMPLE 13

Formulation of clay with a heteroaromatic phthalonitrile based on 1,3-dihydroxypyrimidine and 4-nitrophthalonitrile by physical mixing—To the heteroaromatic phthalonitrile from Example 1 was added various amounts of clay (hydrated aluminum silicate; 0.01 to 20 weight %). Thorough mixing was followed by degassing at 200° C. Then 3-5 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 445° C. before a weight loss was detected. Catastrophic decomposition occurred after 500° C. in air.

EXAMPLE 14

Formulation of boric acid with a heteroaromatic phthalonitrile based on 1,3-dihydroxypyrimidine and 4-nitrophthalonitrile by physical mixing—To the heteroaromatic phthalonitrile from Example 1 was added various amount of boric acid (0.01 to 40 weight %). Thorough mixing was followed by almost immediate curing. The mixture was further cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 460° C. before a weight loss was detected. Catastrophic decomposition occurred after 500° C. in air.

EXAMPLE 15

Synthesis of 2:1 oligomeric heteroaromatic phthalonitrile based on 1,3-dihydroxypyrimidine and 1,4-dibromobenzene—To a 100 mL, three-necked flask fitted with a thermometer, a Dean-Stark trap with condenser, and a nitrogen inlet were added 1,3-dihydroxypyrimidine (5.00 g, 44.6 mmol), 1,4-dibromobenzene (5.21 g, 22.1 mmol), $(PPh_3)_3CuBr$ (0.2 g), powdered anhydrous $K_2CO_3$ (12.3 g, 89.1 mmol), toluene (10 mL), and N,N-dimethylformamide (DMF) (75 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and to monitor the formation of the desired oligomeric product. Toluene was then removed by distillation and the reaction mixture was cooled to 50° C. At this time, 4-nitrophthalonitrile (7.78 g, 44.9 mmol) was added in one portion and the reaction mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric heteroaromatic phthalonitrile (11.00 g, 91% yield). IR $[cm^{-1}]$: $\delta$ 3075 (C=CH), 2232 (C≡N), 1600 (C=N), 1585 (C=C), 1477 (aromatic), 1308 (aromatic), 1244 (C—O), 1172 (C—O), 975 (C—O), 837 (aromatic).

EXAMPLE 16

Curing of 2:1 oligomeric heteroaromatic phthalonitrile based on 1,3-dihydroxypyrimidine and 1,4-dibromobenzene with an aromatic amine—Samples containing the 2:1 oligomeric heteroaromatic phthalonitrile from Example 15 and 2-3 weight % of p-BPAS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 450° C. before any weight loss was detected. Catastrophic decomposition occurred after 500° C.

EXAMPLE 17

Synthesis of 3:2 oligomeric heteroaromatic phthalonitrile based on 1,3-dihydroxypyrimidine and 1,3-dibromobenzene—To a 100 mL, three-necked flask fitted with a thermometer, a Dean-Stark trap with condenser, and a nitrogen inlet were added 1,3-dihydroxypyrimidine (5.00 g, 44.6 mmol), 1,3-dibromobenzene (7.02 g, 29.7 mmol), $(PPh_3)_3CuBr$ (0.2 g), powdered anhydrous $K_2CO_3$ (12.3 g, 89.1 mmol), toluene (10 mL), and N,N-dimethylformamide (DMF) (75 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and to monitor the formation of the desired oligomeric product. Toluene was then removed by distillation and the reaction mixture was cooled to 50° C. At this time, 4-nitrophthalonitrile (5.32 g, 30.2 mmol) was added in one portion and the reaction mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 3:2 oligomeric heteroaromatic phthalonitrile (8.89 g, 80% yield). IR $[cm^{-1}]$: $\delta$ 3075 (C=CH), 2232 (C≡N), 1600 (C=N), 1585 (C=C), 1477 (aromatic), 1308 (aromatic), 1244 (C—O), 1172 (C—O), 975 (C—O), 837 (aromatic).

EXAMPLE 18

Curing of 3:2 oligomeric heteroaromatic phthalonitrile based on 1,3-dihydroxypyrimidine and 1,3-dibromobenzene with an aromatic amine—Samples containing the 3:2 oligomeric heteroaromatic phthalonitrile from Example 17 and 2-3 weight % of p-BPAS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 450° C. before any weight loss was detected. Catastrophic decomposition occurred after 500° C.

EXAMPLE 19

Synthesis of 2:1 oligomeric heteroaromatic phthalonitrile based on bisphenol A and 2,5-dibromothiophene—To a 100 mL, three-necked flask fitted with a thermometer, a Dean-Stark trap with condenser, and a nitrogen inlet were added bisphenol A (5.00 g, 22.0 mmol), 2,5-dibromothiophene (2.62 g, 10.8 mmol), $(PPh_3)_3CuBr$ (0.2 g), powdered anhydrous $K_2CO_3$ (6.00 g, 43.5 mmol), toluene (10 mL), and N,N-dimethylformamide (DMF) (70 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and to monitor the formation of the desired oligomeric product. Toluene was then removed by distillation and the reaction mixture was cooled to 50° C. At this time, 4-nitrophthalonitrile (3.82 g, 22.1 mmol) was added in one portion and the reaction mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric heteroaromatic phthalonitrile (6.32 g, 73% yield). IR [cm$^{-1}$]: δ 3075 (C=CH), 2969 (CH$_3$), 2232 (C≡N), 1585 (C=C), 1530 (S—C), 1477 (aromatic), 1410 (S—C), 1308 (aromatic), 1244 (C—O), 1172 (C—O), 975 (C—O), 837 (aromatic).

EXAMPLE 20

Curing of 2:1 oligomeric heteroaromatic phthalonitrile based on bisphenol A and 2,5-dibromothiophene with an aromatic amine—Samples containing the 2:1 oligomeric heteroaromatic phthalonitrile from Example 19 and 2-3 weight % of p-BPAS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 475° C.

Figure 2:
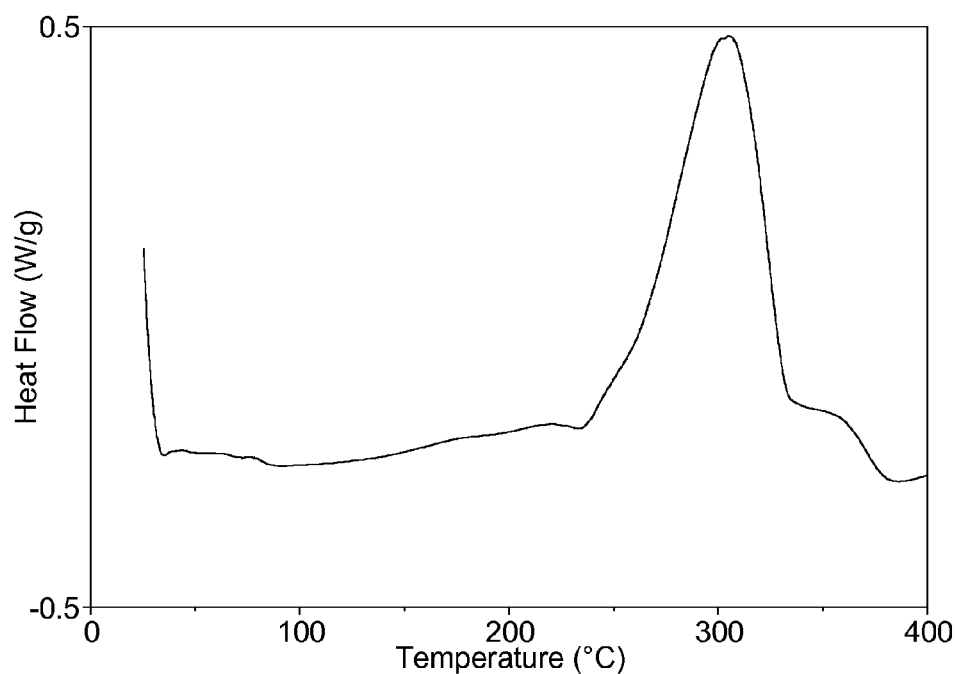
FIG. 2 shows a DSC of the phthalonitrile of Example 19 heated with 5% p-BAPS.

A polymerization study of the phthalonitrile was achieved by DSC analyses (FIG. 2) up to 400° C. in the presence of 5 weight % of p-BAPS to afford the corresponding thermoset. Endothermic and exothermic transitions appeared at 80 and 300° C., respectively, attributed to the glass transition temperature (T$_g$) and the polymerization reaction. The phthalonitrile exhibited a low softening temperature, was completely free flowing around 150° C. (as determined by a visual melting test) and had a long processing window (~100° C.) before reaction with the curing additive occurred to afford the thermoset.

EXAMPLE 21

Synthesis of 2:1 oligomeric heteroaromatic phthalonitrile based on resorcinol and 2,5-dibromothiophene—To a 100 mL, three-necked flask fitted with a thermometer, a Dean-Stark trap with condenser, and a nitrogen inlet were added resorcinol (5.00 g, 45.4 mmol), 2,5-dibromothiophene (5.49 g, 22.7 mmol), (PPh$_3$)$_3$CuBr (0.2 g), powdered anhydrous K$_2$CO$_3$ (8.22 g, 113 mmol), toluene (25 mL), and N,N-dimethylformamide (DMF) (100 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and to monitor the formation of the desired oligomeric product. Toluene was then removed by distillation and the reaction mixture was cooled to 50° C. At this time, 4-nitrophthalonitrile (3.90 g, 22.5 mmol) was added in one portion and the reaction mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric heteroaromatic phthalonitrile (8.81 g, 85% yield). IR [cm$^{-1}$]: δ 3075 (C=CH), 2232 (C≡N), 1585 (C=C), 1530 (S—C), 1477 (aromatic), 1410 (S—C), 1308 (aromatic), 1244 (C—O), 1172 (C—O), 975 (C—O), 837 (aromatic).

EXAMPLE 22

Curing of 2:1 oligomeric heteroaromatic phthalonitrile based on resorcinol and 2,5-dibromothiophene with an aromatic amine—Samples containing the 2:1 oligomeric heteroaromatic phthalonitrile from Example 21 and 2-3 weight % of p-BPAS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 475° C.

EXAMPLE 23

Synthesis of 2:1 oligomeric heteroaromatic phthalonitrile based on 2,5-dihydroxythiophene and 1,3-dibromobenzene—To a 100 mL, three-necked flask fitted with a thermometer, a Dean-Stark trap with condenser, and a nitrogen inlet were added 2,5-dihydroxythiophene (5.00 g, 43.1 mmol), 1,3-dibromobenzene (5.03 g, 21.3 mmol), (PPh$_3$)$_3$CuBr (0.2 g), powdered anhydrous K$_2$CO$_3$ (14.8 g, 108 mmol), toluene (25 mL), and N,N-dimethylformamide (DMF) (100 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and to monitor the formation of the desired oligomeric product. Toluene was then removed by distillation and the reaction mixture was cooled to 50° C. At this time, 4-nitrophthalonitrile (13.1 g, 75.6 mmol) was added in one portion and the reaction mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric heteroaromatic phthalonitrile (9.40 g, 90% yield). IR [cm$^{-1}$]: δ 3075 (C=CH), 2232 (C≡N), 1585 (C=C), 1530 (S—C), 1477 (aromatic), 1410 (S—C), 1308 (aromatic), 1244 (C—O), 1172 (C—O), 975 (C—O), 837 (aromatic).

EXAMPLE 24

Curing of 2:1 oligomeric heteroaromatic phthalonitrile based on 2,5-dihydroxythiophene and 1,3-dibromobenzene with an aromatic amine—Samples containing the 2:1 oligomeric heteroaromatic phthalonitrile from Example 23 and 2-3 weight % of p-BPAS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 425° C. before any weight loss was detected. Catastrophic decomposition occurred after 475° C.

EXAMPLE 25

Synthesis of 2:1 oligomeric heteroaromatic phthalonitrile based on 2,6-dihydroxypyridine and 2,5-dibromothiophene—To a 100 mL, three-necked flask fitted with a thermometer, a Dean-Stark trap with condenser, and a nitrogen inlet were added 2,6-dihydroxypyridine (5.00 g, 45.0 mmol), 2,5-dibromothiophene (5.46 g, 90.9 mmol), $(PPh_3)_3CuBr$ (0.2 g), powdered anhydrous $K_2CO_3$ (15.5 g, 113 mmol), toluene (30 mL), and N,N-dimethylformamide (DMF) (120 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and to monitor the formation of the desired oligomeric product. Toluene was then removed by distillation and the reaction mixture was cooled to 50° C. At this time, 4-nitrophthalonitrile (7.87 g, 45.4 mmol) was added in one portion and the reaction mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric heteroaromatic phthalonitrile (12.44 g, 80% yield). IR [cm$^{-1}$]: δ 3075 (C=CH), 2232 (C≡N), 1600 (C=N), 1585 (C=C), 1530 (S—C), 1477 (aromatic), 1410 (S—C), 1308 (aromatic), 1244 (C—O), 1172 (C—O), 975 (C—O), 837 (aromatic).

EXAMPLE 26

Curing of 2:1 oligomeric heteroaromatic phthalonitrile based on 2,6-dihydroxypyridine and 2,5-dibromothiophene with an aromatic amine—Samples containing the 2:1 oligomeric heteroaromatic phthalonitrile from Example 25 and 2-3 weight % of p-BPAS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 450° C. before any weight loss was detected. Catastrophic decomposition occurred after 495° C.

EXAMPLE 27

Synthesis of 2:1 oligomeric heteroaromatic phthalonitrile based on 2,6-dihydroxypyridine and 1,3-dibromobenzene—To a 100 mL, three-necked flask fitted with a thermometer, a Dean-Stark trap with condenser, and a nitrogen inlet were added 2,6-dihydroxypyridine (5.00 g, 45.0 mmol), 1,3-dibromobenzene (5.31 g, 22.5 mmol), $(PPh_3)_3CuBr$ (0.2 g), powdered anhydrous $K_2CO_3$ (15.5 g, 113 mmol), toluene (10 mL), and N,N-dimethylformamide (DMF) (50 mL). The resulting mixture was degassed with argon at ambient temperature and the Dean-Stark trap was filled with toluene. The mixture was refluxed at 135-145° C. under an argon atmosphere for 12 to 18 h or until no more water was observed being collected in the Dean-Stark trap. FTIR spectroscopy was used to confirm and to monitor the formation of the desired oligomeric product. Toluene was then removed by distillation and the reaction mixture was cooled to 50° C. At this time, 4-nitrophthalonitrile (7.55 g, 43.6 mmol) was added in one portion and the reaction mixture was heated at 80° C. for 6-8 h. The mixture was allowed to cool to ambient temperature and poured into a 5% aqueous HCl solution resulting in the precipitation of a solid. The material was broken up and collected using a Buchner funnel. The white solid was dissolved in chloroform (200 mL), and washed with 200 mL of a 5% aqueous KOH solution, with 200 mL of distilled water until neutral, with 200 mL of a 5% aqueous HCl solution, and finally with 200 mL of water until neutral. The solvent was removed in vacuo and the solid was vacuum dried to yield the 2:1 oligomeric heteroaromatic phthalonitrile (10.7 g, 90% yield). IR [cm$^{-1}$]: δ 3075 (C=CH), 2232 (C≡N), 1603 (C=N), 1585 (C=C), 1477 (aromatic), 1310 (aromatic), 1244 (C—O), 1172 (C—O), 975 (C—O), 835 (aromatic).

EXAMPLE 28

Curing of 2:1 oligomeric heteroaromatic phthalonitrile based on 2,6-dihydroxypyridine and 1,3-dibromobenzene with an aromatic amine—Samples containing the 2:1 oligomeric heteroaromatic phthalonitrile from Example 27 and 2-3 weight % of p-BPAS or m-APB were stirred at 200° C. for 2 minutes and cured under nitrogen by heating at 270° C. for 12 h (overnight), 300° C. for 4 h, 350° C. for 4 h, and 375° C. for 8 h to afford a polymer. The polymers exhibited excellent thermal and oxidative stability up to 450° C. before any weight loss was detected. Catastrophic decomposition occurred after 500° C.

EXAMPLE 29

Formulation of carbon nanotubes with a 2:1 oligomeric heteroaromatic phthalonitrile based on 1,3-dihydroxypyrimidine and 1,4-dibromobenzene in a solvent—To a mixture of the 2:1 oligomeric heteroaromatic phthalonitrile from Example 15 in an appropriate solvent was added various amounts of carbon nanotubes (0.01 to 20 weight %). The mixture was thoroughly mixed. The solvent was removed and the mixture was heated and degassed at 200° C. Then 3 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric compositions exhibited excellent thermal and oxidative stability up to 425-450° C. before any weight loss was detected. Catastrophic decomposition occurred after 500° C. in air.

EXAMPLE 30

Formulation of clay with a 2:1 oligomeric heteroaromatic phthalonitrile based on 1,3-dihydroxypyrimidine and 1,4-dibromobenzene in a solvent—To a mixture of the 2:1 oligomeric heteroaromatic phthalonitrile from Example 15 in an appropriate solvent was added various amount of clay (hydrated aluminum silicate; 0.01 to 20 weight %). The resulting mixtures were thoroughly mixed. The solvent was removed and the mixture was heated and degassed at 200° C. Then 3-4 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 430-460° C. before any weight loss was detected. Catastrophic decomposition occurred after 500° C. in air.

EXAMPLE 31

Formulation of carbon nanofibers with a 2:1 oligomeric heteroaromatic phthalonitrile based on 1,3-dihydroxypyrimidine and 1,4-dibromobenzene in a solvent—To a mixture of the 2:1 oligomeric heteroaromatic phthalonitrile from Example 15 in an appropriate solvent was added various amounts of carbon nanofibers (0.01 to 20 weight %). The mixtures were thoroughly mixed by stirring. The solvent was removed and the mixture heated and degassed at 200° C. Then 4 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 425-450° C. before any weight loss was detected. Catastrophic decomposition occurred after 500° C. in air.

EXAMPLE 32

Formulation of a metal oxide with 2:1 oligomeric heteroaromatic phthalonitrile based on 1,3-dihydroxypyrimidine and 1,4-dibromobenzene in a solvent—To a mixture of the 2:1 oligomeric heteroaromatic phthalonitrile from Example 15 in an appropriate solvent was added various amount of powdered zinc oxide (0.01 to 20 weight %) with thorough mixing. The solvent was removed and the mixture was heated and degassed at 200° C. Then 4-5 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 450° C. before a weight loss was detected. Catastrophic decomposition occurred after 500° C. in air.

EXAMPLE 33

Formulation of clay with a 2:1 oligomeric heteroaromatic phthalonitrile based on 1,3-dihydroxypyrimidine and 1,4-dibromobenzene by physical mixing—To the 2:1 oligomeric heteroaromatic phthalonitrile from Example 15 was added various amount of clay (hydrated aluminum silicate; 0.01 to 20 weight %). Thorough physical mixing was followed by degassed at 200° C. Then 3-5 weight % of p-BPAS or m-APB was stirred in at 200° C. for 2 minutes and the mixture was cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 450° C. before a weight loss was detected. Catastrophic decomposition occurred after 500° C. in air.

EXAMPLE 34

Formulation of boric acid with a 2:1 oligomeric heteroaromatic phthalonitrile based on 1,3-dihydroxypyrimidine and 1,4-dibromobenzene by physical mixing—To the 2:1 oligomeric heteroaromatic phthalonitrile from Example 15 was added various amount of boric acid (0.01 to 40 weight %). Thorough mixing was followed by almost immediate curing. The mixture was further cured under nitrogen by heating at 270° C. for 12 h (overnight), 300° C. for 4 h, 350° C. for 4 h, and 375° C. for 8 h to afford a polymer. The polymeric mixtures or compositions exhibited excellent thermal and oxidative stability up to 460° C. before a weight loss was detected. Catastrophic decomposition occurred after 500° C. in air.

EXAMPLE 35

Synthesis of 1/20 molar mixture of octacarbonyldicobalt and a heteroaromatic phthalonitrile based on 1,3-dihydroxypyrimidine and 4-nitrophthalonitrile—$Co_2(CO)_8$ (47 mg, 0.137 mmol), heteroaromatic phthalonitrile (1.00 g, 2.74 mmol) and 10 ml of methylene chloride were added to a 50 ml round bottomed flask. The homogeneous mixture was allowed to stir for 1 h before the solvent was removed under reduced pressure. The mixture was vacuum dried to yield a dark solid.

EXAMPLE 36

Thermal conversion of 1/20 molar mixture of octacarbonyldicobalt and a heteroaromatic phthalonitrile based on 1,3-dihydroxypyrimidine and 4-nitrophthalonitrile to carbon nanotube-cobalt nanoparticle composition—The mixture from Example 35 (25 mg) was heated in a TGA chamber under nitrogen at 10° C./min to 1000° C. resulting in a shaped composition and a char yield of 80%. X-ray studies confirm the presence of carbon nanotubes-cobalt nanoparticles in the carbon composition. The x-ray diffraction study showed the four characteristic reflections [(002), (100), (004), and (110)] values for crystalline carbon nanotubes and the pattern for cobalt nanoparticles.

Figure 3:
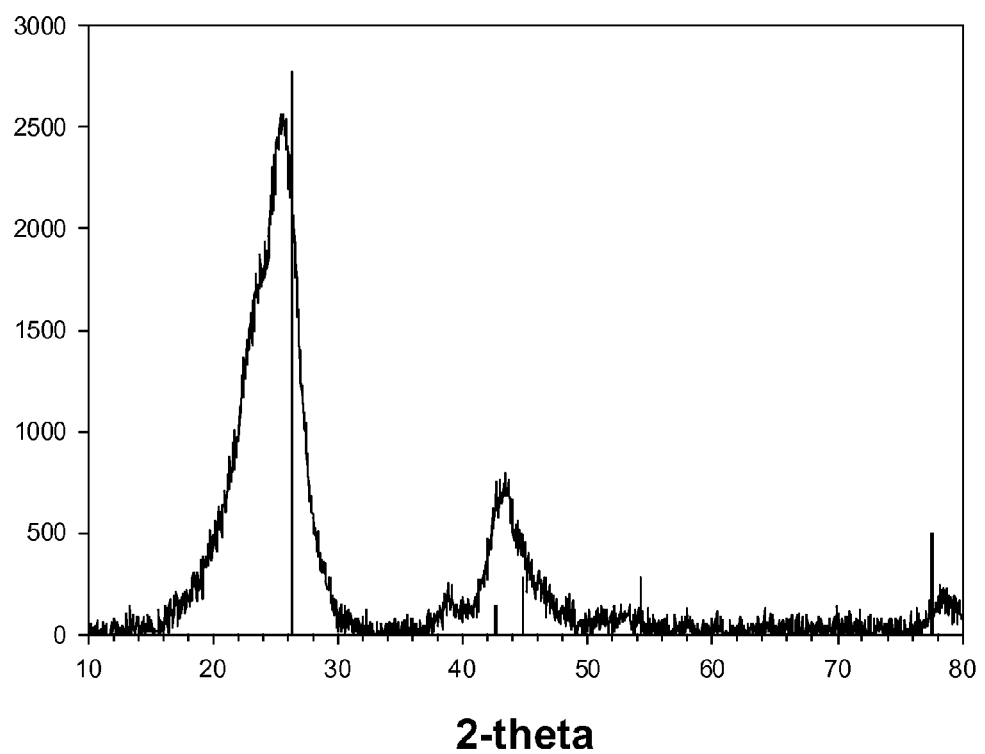
FIG. 3 shows a XRD showing the presence of CNTs/CNFs in a sample of the nitrogen heteroaromatic-containing phthalonitrile of Example 1 heated to 1000° C. in the presence of $Fe_2(CO)_9$.

X-ray analysis (FIG. 3) shows the presence of carbon nanotubes in the developing carbonaceous system when heated to 1000° C. with the characteristic graphite (002) peak (CNT) appearing around 25.9. Only a trace amount of transition metal (Co, Ni, and Fe) appeared to be needed to ensure the formation of CNTs. As the temperature of the carbonaceous system was increased, higher concentrations and yields of CNTs were formed.

EXAMPLE 37

Synthesis of 1/40 molar mixture of octacarbonyldicobalt and a heteroaromatic phthalonitrile based on 1,3-dihydroxypyrimidine and 4-nitrophthalonitrile—$Co_2(CO)_8$ (23 mg, 0.069 mmol), heteroaromatic phthalonitrile (1.00 g, 2.74 mmol) and 10 ml of methylene chloride were added to a 50 ml round bottomed flask. The homogeneous mixture was allowed to stir for 1 h before the solvent was removed under reduced pressure. The mixture was vacuum dried to yield a dark solid.

EXAMPLE 38

Thermal conversion of 1/40 molar mixture of octacarbonyldicobalt and a heteroaromatic phthalonitrile based on 1,3- dihydroxypyrimidine and 4-nitrophthalonitrile to carbon nanotube-cobalt nanoparticle composition—The mixture from Example 37 (50 mg) was heated in a TGA chamber under nitrogen at 10° C./min to 1000° C. resulting in a shaped composition and a char yield of 80%. X-ray studies confirm the presence of carbon nanotubes-cobalt nanoparticles in the carbon composition. The x-ray diffraction study showed the four characteristic reflections [(002), (100), (004), and (110)] values for crystalline carbon and the pattern for cobalt nanoparticles

EXAMPLE 39

Synthesis of 1/10 molar mixture of octacarbonyldicobalt and a heteroaromatic phthalonitrile based on 1,3-dihydroxypyrimidine and 4-nitrophthalonitrile—$Co_2(CO)_8$ (94 mg, 0.274 mmol), heteroaromatic phthalonitrile (1.00 g, 2.74 mmol) and 10 ml of methylene chloride were added to a 50 ml round bottomed flask. The homogeneous mixture was allowed to stir for 1 h before the solvent was removed under reduced pressure. The mixture was vacuum dried to yield a dark solid.

EXAMPLE 40

Thermal conversion of 1/10 molar mixture of octacarbonyldicobalt and a heteroaromatic phthalonitrile based on 1,3-dihydroxypyrimidine and 4-nitrophthalonitrile to carbon nanotube-cobalt nanoparticle composition—The mixture from Example 39 (50 mg) was heated in a TGA chamber under nitrogen at 10° C./min to 1000° C. resulting in a shaped composition and a char yield of 75%. X-ray studies confirm the presence of carbon nanotubes-cobalt nanoparticles in the carbon composition. The x-ray diffraction study showed the four characteristic reflections [(002), (100), (004), and (110)] values for crystalline carbon nanotubes and the pattern for cobalt nanoparticles

EXAMPLE 41

Synthesis of 1/20 molar mixture of iron carbonyl and a heteroaromatic phthalonitrile based on 1,3-quinolinediol and 4-nitrophthalonitrile—$Fe_2(CO)_9$ (44 mg, 0.121 mmol), heteroaromatic phthalonitrile (1.00 g, 2.42 mmol) and 10 ml of chloroform were added to a 50 ml round bottomed flask. The homogeneous mixture was allowed to stir for 1 h before the solvent was removed under reduced pressure. The mixture was vacuum dried to yield a dark solid.

EXAMPLE 42

Thermal conversion of 1/20 molar mixture of iron carbonyl and a heteroaromatic phthalonitrile based on 1,3-quinolinediol and 4-nitrophthalonitrile to carbon nanotube-cobalt nanoparticle composition—The mixture from Example 41 (47 mg) was heated in a TGA chamber under nitrogen at 10° C./min to 1000° C. resulting in a shaped composition and a char yield of 81%. X-ray studies confirm the presence of carbon nanotubes-iron nanoparticles in the carbon composition. The x-ray diffraction study showed the four characteristic reflections [(002), (100), (004), and (110)] values for crystalline carbon nanotubes and the pattern for cobalt nanoparticles

EXAMPLE 43

Synthesis of 1/10 molar mixture of nickel cyclooctadiene and a heteroaromatic phthalonitrile based on 1,3-quinolinediol and 4-nitrophthalonitrile—Nickel cyclooctadiene (67 mg, 0.242 mmol), heteroaromatic phthalonitrile (1.00 g, 2.42 mmol) and 10 ml of methylene chloride were added to a 50 ml round bottomed flask. The homogeneous mixture was allowed to stir for 2 h before the solvent was removed under reduced pressure. The mixture was vacuum dried to yield a dark solid.

EXAMPLE 44

Thermal conversion of 1/10 molar mixture of nickel cyclooctadiene and a heteroaromatic phthalonitrile based on 1,3-quinolinediol and 4-nitrophthalonitrile to carbon nanotube-cobalt nanoparticle composition—The mixture from Example 43 (22 mg) was heated in a TGA chamber under nitrogen at 10° C./min to 1000° C. resulting in a shaped composition and a char yield of 78%. X-ray studies confirm the presence of carbon nanotubes-nickel nanoparticles in the carbon composition. The x-ray diffraction study showed the four characteristic reflections [(002), (100), (004), and (110)] values for crystalline carbon nanotubes and the pattern for nickel nanoparticles

EXAMPLE 45

Synthesis of 1/20 molar mixture of octacarbonyldicobalt, copper acetylacetonate and a heteroaromatic phthalonitrile based on 1,3-quinolinediol and 4-nitrophthalonitrile—$Co_2(CO)_8$ (44 mg, 0.121 mmol), Cu acetylacetonate (32 mg, 0.121 mmol), heteroaromatic phthalonitrile (1.00 g, 2.42 mmol) and 10 ml of chloroform were added to a 50 ml round bottomed flask. The homogeneous mixture was allowed to stir for 1 h before the solvent was removed under reduced pressure. The mixture was vacuum dried to yield a dark solid.

EXAMPLE 46

Thermal conversion of 1/20 molar mixture of octacarbonyldicobalt, copper acetylacetonate and a heteroaromatic phthalonitrile based on 1,3-quinolinediol and 4-nitrophthalonitrile to carbon nanotube-cobalt nanoparticle composition—The mixture from Example 45 (55 mg) was heated in a TGA chamber under nitrogen at 10° C./min to 1000° C. resulting in a shaped composition and a char yield of 73%. X-ray studies confirm the presence of carbon nanotubes-cobalt-copper nanoparticles in the carbon composition. The x-ray diffraction study showed the four characteristic reflections [(002), (100), (004), and (110)] values for crystalline carbon nanotubes and the pattern for cobalt and copper nanoparticles

EXAMPLE 47

Synthesis of 1/20 molar mixture of octacarbonyldicobalt, copper acetylacetonate and a heteroaromatic phthalonitrile based on 1,3-quinolinediol and 4-nitrophthalonitrile and an aromatic amine—$Co_2(CO)_8$ (44 mg, 0.121 mmol), Cu acetylacetonate (32 mg, 0.121 mmol), heteroaromatic phthalonitrile (1.00 g, 2.42 mmol), p-BPAS (50 mg, 5 wt %) and 10 ml of chloroform were added to a 50 ml round bottomed flask. The homogeneous mixture was allowed to stir for 1 h before the solvent was removed under reduced pressure. The mixture was vacuum dried to yield a dark solid.

EXAMPLE 48

Thermal conversion of 1/20 molar mixture of octacarbonyldicobalt, copper acetylacetonate and a heteroaromatic phthalonitrile based on 1,3-quinolinediol and 4-nitrophthalonitrile and an aromatic amine to carbon nanotube-cobalt nanoparticle composition—The mixture from Example 47 (100 mg) was heated on a hot plate to 300° C. until the monomer polymerized (10 min). A piece of the aforementioned polymer (50 mg) was heated in a TGA chamber under nitrogen at 10° C./min to 1000° C. resulting in a shaped composition and a char yield of 73%. X-ray studies confirm the presence of carbon nanotubes-cobalt-copper nanoparticles in the carbon composition. The x-ray diffraction study showed the four characteristic reflections [(002), (100), (004), and (110)] values for crystalline carbon nanotubes and the pattern for cobalt and copper nanoparticles

EXAMPLE 49

Synthesis of 1/40 molar mixture of octacarbonyldicobalt and a 2:1 oligomeric heteroaromatic phthalonitrile based on bisphenol A and 2,5-dibromothiophene—$Co_2(CO)_8$ (11 mg, 0.032 mmol), heteroaromatic phthalonitrile (1.00 g, 1.26 mmol) and 10 ml of methylene chloride were added to a 50 ml round bottomed flask. The homogeneous mixture was allowed to stir for 1 h before the solvent was removed under reduced pressure. The mixture was vacuum dried to yield a dark solid.

EXAMPLE 50

Thermal conversion of 1/40 molar mixture of octacarbonyldicobalt and a 2:1 oligomeric heteroaromatic phthalonitrile based on bisphenol A and 2,5-dibromothiophene to carbon nanotube-cobalt nanoparticle composition—The mixture from Example 49 (50 mg) was heated in a TGA chamber under nitrogen at 10° C./min to 1000° C. resulting in a shaped composition and a char yield of 83%. X-ray studies confirm the presence of carbon nanotubes-cobalt nanoparticles in the carbon composition. The x-ray diffraction study showed the four characteristic reflections [(002), (100), (004), and (110)] values for crystalline carbon nanotubes and the pattern for cobalt nanoparticles

EXAMPLE 51

Synthesis of 1/40 molar mixture of octacarbonyldicobalt, silver (I) oxide and a 2:1 oligomeric heteroaromatic phthalonitrile based on bisphenol A and 2,5-dibromothiophene—$Co_2(CO)_8$ (11 mg, 0.032 mmol), $Ag_2O$ (7.3 mg, 0.032 mmol) heteroaromatic phthalonitrile (1.00 g, 1.26 mmol) and 10 ml of methylene chloride were added to a 50 ml round bottomed flask. The homogeneous mixture was allowed to stir for 1 h before the solvent was removed under reduced pressure. The mixture was vacuum dried to yield a dark solid.

EXAMPLE 52

Thermal conversion of 1/40 molar mixture of octacarbonyldicobalt, silver (I) oxide and a 2:1 oligomeric heteroaromatic phthalonitrile based on bisphenol A and 2,5-dibromothiophene to carbon nanotube-cobalt nanoparticle composition—The mixture from Example 51 (50 mg) was heated in a TGA chamber under nitrogen at 10° C./min to 1000° C. resulting in a shaped composition and a char yield of 77%. X-ray studies confirm the presence of carbon nanotubes-cobalt-silver nanoparticles in the carbon composition. The x-ray diffraction study showed the four characteristic reflections [(002), (100), (004), and (110)] values for crystalline carbon nanotubes and the pattern for cobalt and silver nanoparticles

EXAMPLE 53

Oxidative purification of a carbon nanotube-cobalt nanoparticle composition derived from a 1/40 molar mixture of octacarbonyldicobalt, silver (I) oxide and a 2:1 oligomeric heteroaromatic phthalonitrile based on bisphenol A and 2,5-dibromothiophene—The carbon nanotube-cobalt-silver nanoparticle composition from Example 54 (100 mg) was heated under air in a muffle furnace at 400° C. for 2 h resulting in a weight loss of 65%. X-ray studies confirm a reduction in the amorphous carbon and the presence of carbon nanotubes-cobalt oxide-silver oxide nanoparticles in the carbon composition.

EXAMPLE 54

Oxidative purification of a carbon nanotube-iron nanoparticle composition derived from a 1/40 molar mixture of iron carbonyl, and heteroaromatic phthalonitrile based on 1,3-quinolinediol and 4-nitrophthalonitrile—The carbon nanotube-iron nanoparticle composition from Example 53 (200 mg) was heated under air in a muffle furnace at 440° C. for 6 h resulting in a weight loss of 55%. X-ray studies confirm a reduction in the amorphous carbon and the presence of carbon nanotubes-iron oxide nanoparticles in the carbon composition.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. An oligomer having the formula:

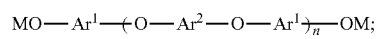

wherein M is a metal or H;
wherein n is an integer greater than or equal to 1;
wherein $Ar^1$ and $Ar^2$ are independently selected aromatic- or heterocyclic-containing groups; and
wherein $Ar^1$, $Ar^2$, or both are heteroaromatic or heterocyclic groups containing a nitrogen, sulfur, or oxygen heteroatom.

2. The oligomer of claim 1, wherein the heteroaromatic or heterocyclic group is a single heteroaromatic ring or is two or more fused aromatic rings containing at least one heteroatom in the fused aromatic rings.

3. The oligomer of claim 1, wherein n is 1 or 2.

4. The oligomer of claim 1, wherein n is greater than or equal to 2.

5. The oligomer of claim 1, wherein the compound is

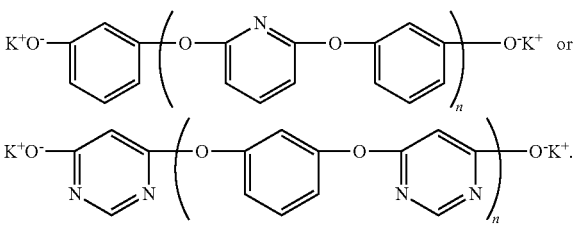

6. The oligomer of claim 1, wherein the compound is
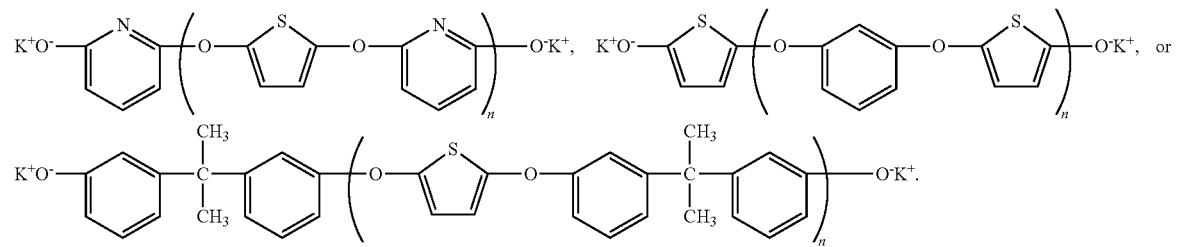
* * * * *